(12) United States Patent
Misawa

(10) Patent No.: US 7,479,640 B2
(45) Date of Patent: Jan. 20, 2009

(54) RESOLUTION-VARIABLE X-RAY IMAGING DEVICE AND X-RAY CT APPARATUS

(75) Inventor: Takeshi Misawa, Saitama (JP)

(73) Assignee: Fujifilm Corporation, Tokyo (JP)

( * ) Notice: Subject to any disclaimer, the term of this patent is extended or adjusted under 35 U.S.C. 154(b) by 42 days.

(21) Appl. No.: 11/528,407

(22) Filed: Sep. 28, 2006

(65) Prior Publication Data

US 2007/0075252 A1 Apr. 5, 2007

(30) Foreign Application Priority Data

Sep. 30, 2005 (JP) ............................ P2005-288864

(51) Int. Cl.
G01T 1/24 (2006.01)
H01L 27/146 (2006.01)

(52) U.S. Cl. ............................ 250/370.09; 250/370.01; 250/370.08; 250/370.11; 250/363.08; 250/363.09

(58) Field of Classification Search ................ 250/300, 250/370.09, 370.11, 363.05, 363.01, 368, 250/370.01, 366, 370.08, 363.02, 363.08, 250/363.09; 378/63, 19, 4, 98.8, 57, 56, 378/59, 60, 65, 69, 75

See application file for complete search history.

(56) References Cited

U.S. PATENT DOCUMENTS

| | | | | |
|---|---|---|---|---|
| 5,970,115 | A * | 10/1999 | Colbeth et al. | 378/62 |
| 5,973,311 | A * | 10/1999 | Sauer et al. | 250/208.1 |
| 6,243,441 | B1 * | 6/2001 | Zur | 378/98.8 |
| 6,864,555 | B2 * | 3/2005 | Worley | 257/435 |
| 7,095,028 | B2 * | 8/2006 | Mollov et al. | 250/370.09 |
| 2003/0015738 | A1 * | 1/2003 | Kwon | 257/233 |
| 2003/0169847 | A1 * | 9/2003 | Karellas et al. | 378/98.3 |
| 2005/0105678 | A1 * | 5/2005 | Nakashima | 378/4 |
| 2005/0205958 | A1 * | 9/2005 | Taniguchi et al. | 257/436 |
| 2005/0218330 | A1 * | 10/2005 | Rose et al. | 250/368 |
| 2007/0075253 | A1 * | 4/2007 | Misawa et al. | 250/370.11 |

FOREIGN PATENT DOCUMENTS

| | | |
|---|---|---|
| JP | 5-152597 | 6/1993 |
| JP | 5-269122 | 10/1993 |
| JP | 6-214036 | 8/1994 |
| JP | 11-151235 | 6/1999 |
| JP | 2000-56028 | 2/2000 |
| JP | 2002-200073 | 7/2002 |
| JP | 2002-306467 | 10/2002 |
| JP | 2003-17676 | 1/2003 |

* cited by examiner

*Primary Examiner*—David P Porta
*Assistant Examiner*—David S Baker
(74) *Attorney, Agent, or Firm*—McGinn IP Law Group, PLLC (57) ABSTRACT

A resolution-variable X-ray imaging device is provided and includes: a scintillator that receives an X-ray through a subject to emit fluorescence; and an imaging device comprising a plurality of pixels aligned at pixel intervals on a light receiving surface of the imaging device, each of the pixels receiving the fluorescence and converting the fluorescence into an electric signal. The imaging device has at least two areas of: a higher-resolution imaging area in which the pixels are aligned at a pixel interval; and a lower-resolution imaging area in which the pixels are aligned at a pixel interval longer than the pixel interval of the higher-resolution imaging area.

14 Claims, 11 Drawing Sheets

SPECTRAL SENSITIVITY CURVE
OF QUINACRIDONE

FIG. 6B

STRUCTURAL FORMULA
OF QUINACRIDONE

RESOLUTION-VARIABLE X-RAY IMAGING DEVICE AND X-RAY CT APPARATUS

BACKGROUND OF THE INVENTION

1. Field of the Invention

The present invention relates to an X-ray imaging device in which the scintillator for converting an X-ray into a visible light, or the like and the imaging devices for receiving the visible light, or the like are used in combination and, more particularly, a resolution-variable X-ray imaging device whose resolution can be changed as occasion demands and an X-ray CT apparatus using the same.

2. Description of Related Art

As the X-ray imaging device for capturing an image by visualizing an X-ray, there are some devices that can sense directly an X-ray and others that can visualize an X-ray by using the scintillator and then capture an image by using the imaging device such as CCD, or the like, as set forth in JP-A-5-152597, JP-A-6-214036, JP-A-11-151235, JP-A-2000-56028 and JP-A-2003-17676.

Figure 10:
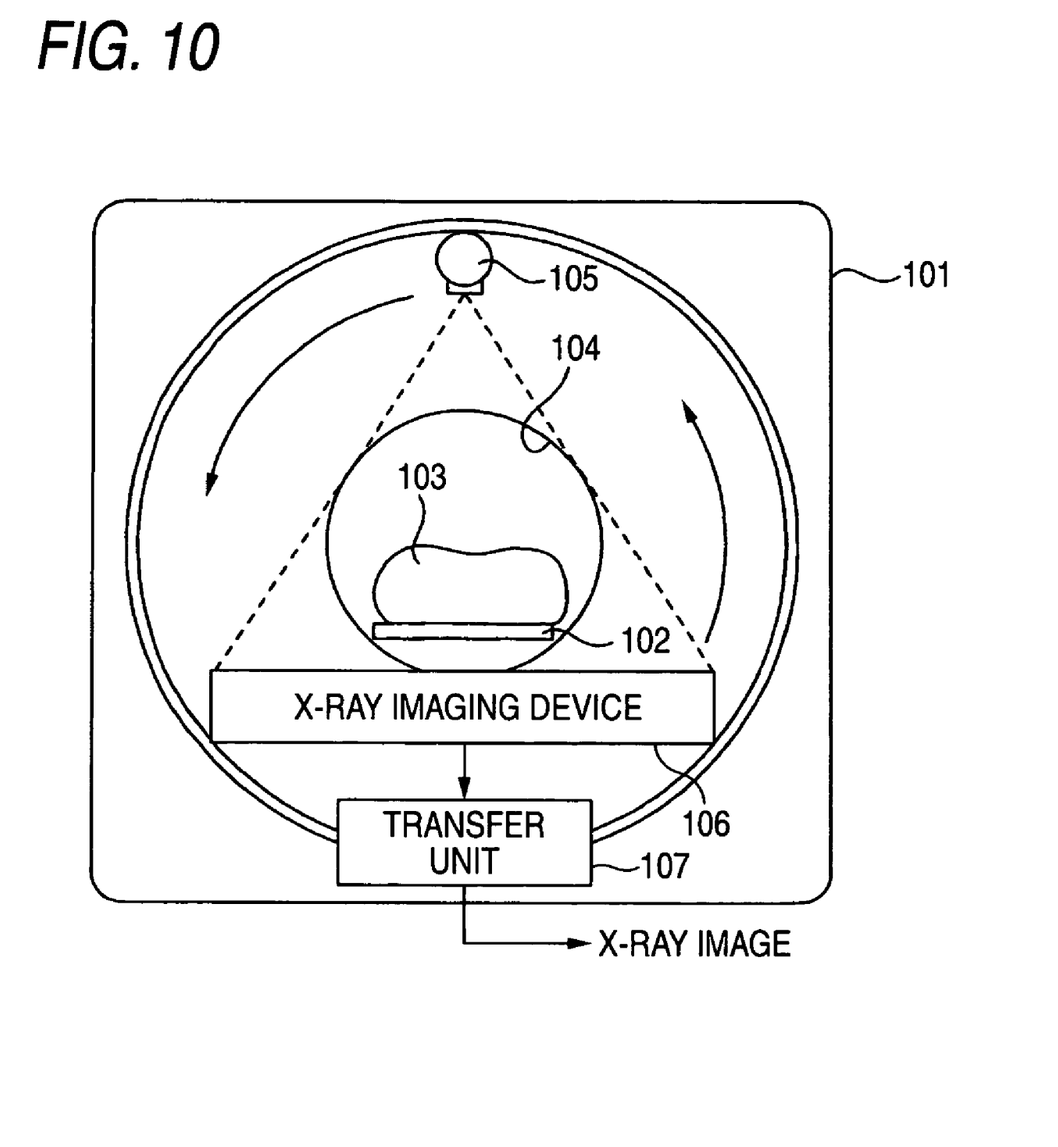
FIG. 10 is an explanatory view of an X-ray CT apparatus in the related art.

When the X-ray (computed tomography) CT apparatus shown in FIG. 10, for example, is constructed by using the scintillator and the imaging device in combination, a circular opening portion 104 into which a subject 103 on a stretcher 102 is carried is provided to a center of a main body of an X-ray CT apparatus 101. An X-ray irradiator 105 for irradiating an X-ray onto the subject 103, an X-ray imaging device (having a scintillator and an imaging device) 106 for receiving the X-ray transmitted through the subject 103, a driving mechanism (not shown) for causing the X-ray irradiator 105 and the X-ray imaging device 106 to turn integrally around the circular opening portion 104, and a transfer unit 107 for transferring the captured image of the subject 103 output from the X-ray imaging device 106 to the outside are provided to the main body of the X-ray CT apparatus 101.

Figure 11:
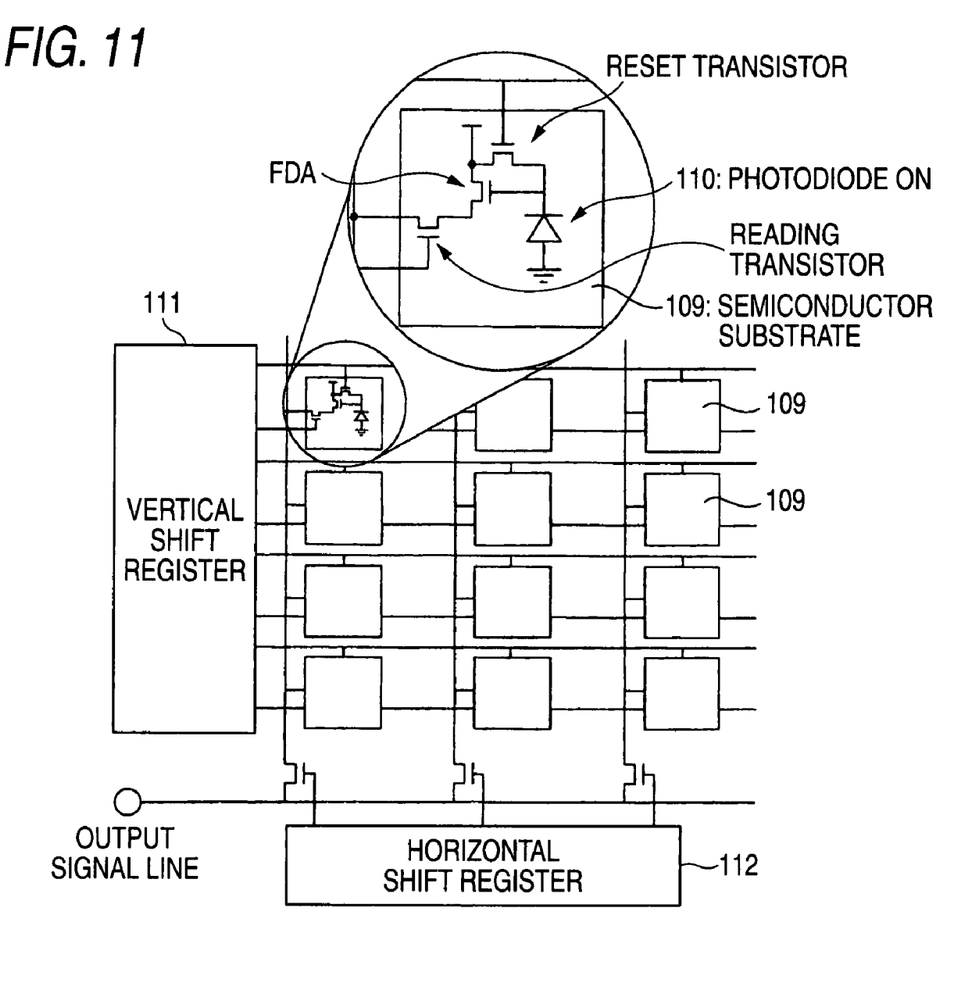
FIG. 11 is a schematic plan view of an X-ray imaging device shown in FIG. 10.

FIG. 11 is a schematic plan view of the X-ray imaging device 106 in the related art. A great number of pixels 109 having a same size are aligned and formed vertically and horizontally at a same pitch respectively on the substrate. Each pixel 109 is constructed by a photodiode 110 formed on the semiconductor substrate, and a signal reading circuit consisting of a reset transistor, FDA, and a reading transistor, which are formed in positions adjacent to this photodiode 110.

The signal reading circuit of each pixel 109 outputs a sensed signal responding to a signal charge stored in the photodiode 110 of the pixel 109 to an output signal line when it is designated by a vertical shift register 111 and a horizontal shift register 112. Then, this sensed signal is output from the X-ray imaging device 106 to the transfer unit 107.

In the X-ray imaging device 106 in the related art, as shown in FIG. 11, since a great number of pixels having the same shape are aligned and formed on the substrate at same pitches, a resolution of the image is fixed basically. That is, the tomogram is captured at the same resolution, no matter which part of the subject 103 the X-ray imaging device 106 is captured.

It is preferable that the X-ray CT apparatus should have a high-resolution X-ray imaging device 106, a driving mechanism and a signal processing mechanism that can be operated at a high scanning rate. In this case, such X-ray CT apparatus becomes inevitably expensive (JP-A-2002-200073, JP-A-5-269122 and JP-A-2002-306467).

With the technical progress in recent years, a resolution of the X-ray imaging device used in the X-ray CT apparatus is increased and also a scanning rate is increased to a higher rate. However, in the configuration of the X-ray imaging device in the related art, even when a portion of the subject whose image needs merely a low resolution is invested, the resolution-fixed imaging device is used to capture the image. Therefore, the image of the corresponding portion of the subject is captured at an excessively high resolution as image data.

If data acquisition at a lower resolution may be allowed, the image data can be acquired at a higher scanning rate correspondingly, and thus an exposure dose of the subject can be reduced. However, the resolution is fixed in the X-ray imaging device in the related art, it is impossible for the user's operation to increase a scanning rate while keeping a low resolution of the image.

SUMMARY OF THE INVENTION

An object of an illustrative, non-limiting embodiment of the present invention is to provide a resolution-variable X-ray imaging device and an X-ray CT apparatus using this X-ray imaging device.

According to one aspect of the invention, there is provided a resolution-variable X-ray imaging device including: a scintillator that receives an X-ray through a subject to emit fluorescence; and an imaging device including a plurality of pixels aligned at pixel intervals on a light receiving surface of the imaging device, each of the pixels receiving the fluorescence and converting the fluorescence into an electric signal. The imaging device has at least two areas of: a higher-resolution imaging area in which the pixels are aligned at a pixel interval; and a lower-resolution imaging area in which the pixels are aligned at a pixel interval longer than the pixel interval of the higher-resolution imaging area.

In one aspect of the invention, the imaging device has a photosensitive layer containing an organic material that photoelectrically converts incident light.

In one aspect of the invention, the scintillator and the photosensitive layer are formed of respective materials such that a peak wavelength of the fluorescence emitted from the scintillator coincides, in a wavelength range, with a peak wavelength of a photo sensitivity of the photosensitive layer.

In one aspect of the invention, each of the higher-resolution imaging area and the lower-resolution imaging has pixel pitches different in two directions of a slice direction and a scan direction (i.e., two directions perpendicular to each other).

In one aspect of the invention, light receiving areas of respective pixels in the two areas are substantially identical. That is, each of the pixels in each of the higher-resolution imaging area and the lower-resolution imaging has a common light receiving area.

According to one aspect of the invention, there is provided an X-ray CT apparatus including: an X-ray irradiator for irradiating a subject with an X-ray; an X-ray imaging device according to one aspect of the invention, positioned opposite to the X-ray irradiator via the subject; and a driving unit for turning integrally the X-ray irradiator and the X-ray imaging device around the subject in such a state that the X-ray irradiator and the X-ray imaging device are opposed to each other.

In one aspect of the invention, the resolution-variable X-ray imaging device has a curved shape.

BRIEF DESCRIPTION OF THE DRAWINGS

The features of the invention will appear more fully upon consideration of the exemplary embodiments of the inventions, which are schematically set forth in the drawings, in which.

DETAILED DESCRIPTION OF THE EXEMPLARY EMBODIMENTS

Although the invention will be described below with reference to the exemplary embodiments thereof, the following exemplary embodiments and modifications do not restrict the invention.

According to exemplary embodiments, since the tomogram of the subject can be captured at different resolutions, a reduction of X-ray exposure dose can be achieved by increasing a scanning rate to a higher scanning rate when the image is captured at a lower resolution.

Exemplary embodiments of the present invention will be explained with reference to the drawings hereinafter.

Figure 1:
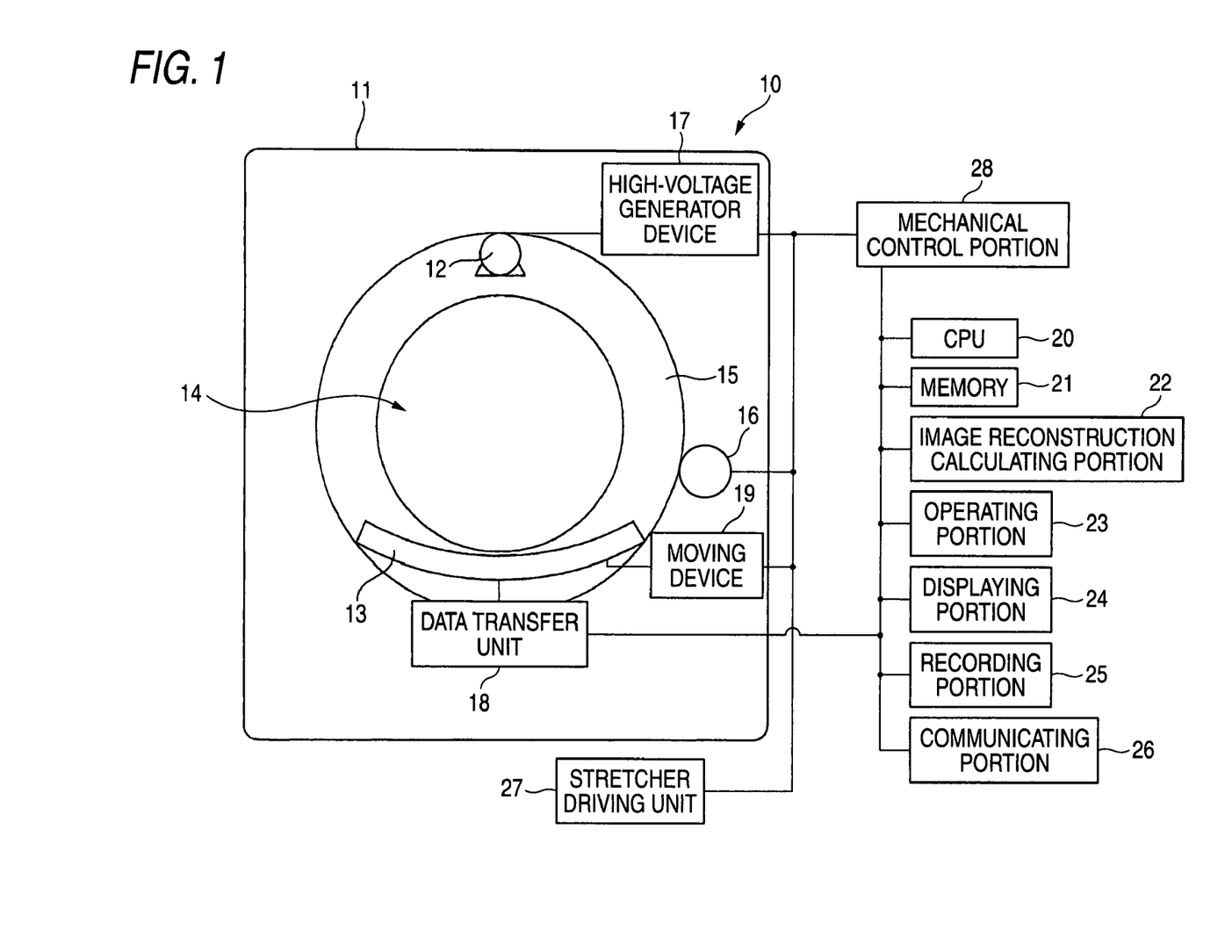
FIG. 1 is a configurative view of an X-ray CT apparatus according to an exemplary embodiment of the present invention.

FIG. 1 is a configurative view of an X-ray CT apparatus according to an exemplary embodiment of the present invention. An X-ray CT apparatus 10 includes a main body 11 of the apparatus, an X-ray irradiator 12 provided in the main body 11 of the apparatus, a resolution-variable X-ray imaging device 13 arranged opposite to the X-ray irradiator 12 and to be curved, a frame 15 for causing the X-ray irradiator 12 and the X-ray imaging device 13 to turn together around a center opening portion 14, a frame driving portion 16 for driving the frame 15 to turn, a high-voltage generator device 17 for supplying a high voltage to the X-ray irradiator 12 via a slip ring, a data transfer unit 18 for transferring X-ray captured image data output from the X-ray imaging device 13, and a moving device 19 for moving the X-ray imaging device 13 to shift an X-ray receiving position.

As the resolution-variable X-ray imaging device 13 of the present embodiment, the curved X-ray imaging device 13 is employed as illustrated, but the flat-plate X-ray imaging device may be employed. The reason why the curved X-ray imaging device 13 is employed is to attain a size reduction of the main body 11 of the X-ray CT apparatus. The moving device 19 is used to move an X-ray receiving position of the X-ray imaging device 13 to either a higher-resolution image imaging area A or a lower-resolution image imaging area B, as described later.

This X-ray CT apparatus 10 further includes a CPU 20 for controlling the overall X-ray CT apparatus 10, a memory 21, an image reconstruction calculating portion 22, an operating portion 23, a displaying portion 24 for displaying the X-ray captured image data sent from the data transfer unit 18, a recording portion 25 for recording the captured image data, a communicating portion 26, a stretcher driving unit 27, and a mechanical control portion 28 for controlling the high-voltage generator device 17, the frame driving portion 16, the stretcher driving unit 27, and the moving device 19.

Figure 2:
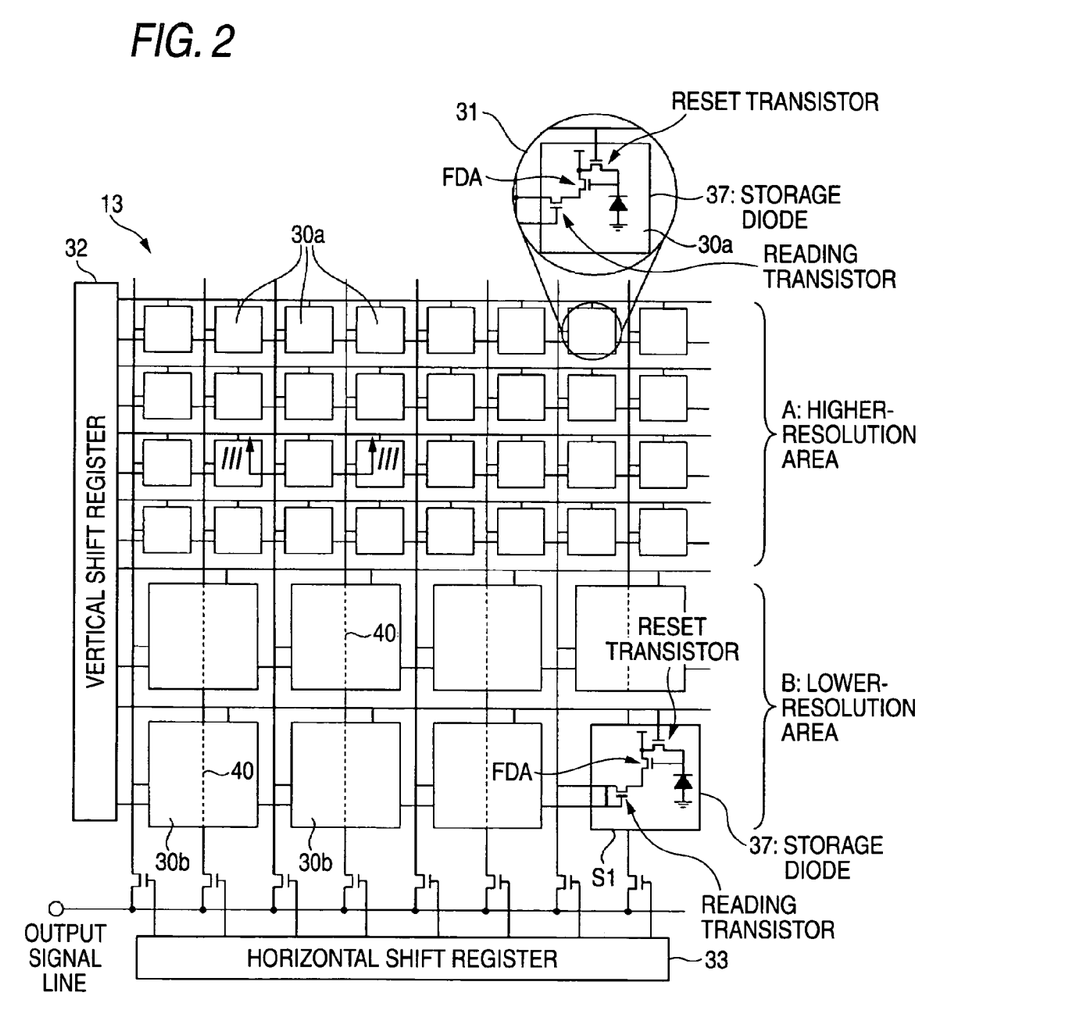
FIG. 2 is a schematic view of an X-ray imaging device shown in FIG. 1, a part of which is shown in an enlarged unpackaged manner.

FIG. 2 is a schematic view of the X-ray imaging device 13 shown in FIG. 1, a part of which is shown in an enlarged unpackaged manner. In the illustrated example, the higher-resolution image imaging area A and the lower-resolution image imaging area B are provided in the resolution-variable X-ray imaging device 13 of the present embodiment. A higher-resolution image is captured when the X-ray is received by the higher-resolution image imaging area A, while a lower-resolution image is captured when the X-ray is received by the lower-resolution image imaging area B.

A large number of pixels 30a are aligned and formed at a narrow pitch in the higher-resolution image imaging area A. Also, a large number of pixels 30b are aligned and formed at a wide pitch in the lower-resolution image imaging area B.

In the illustrated example, a light receiving area (shown by a square) of the pixel 30b provided in the lower-resolution image imaging area B is about four times wider than a light receiving area of the pixel 30a provided in the higher-resolution image imaging area A. In this event, the light receiving area of the pixel 30b may be set equal to that of the pixel 30a, and it may be set arbitrarily that to what extent the light receiving area should be widened and in what shape respective pixels should be formed.

A charge storage diode 37 for storing a signal charge that each pixel 30a, 30b receives, and a signal reading circuit 31 for reading an image signal in response to the signal charge are formed on bottom portions of respective pixels 30a, 30b.

In the present embodiment, a signal reading circuit constructed by three transistors used in the CMOS image sensor is shown as an example of the signal reading circuit 31, but a signal reading circuit constructed by four transistors may be employed. When the signal reading circuit corresponding to the pixel from which the pixel signal is to be read is designated by a vertical shift register 32 and a horizontal shift register 33, an image signal is output from the X-ray imaging device 13 to the data transfer unit 18.

Figure 3:
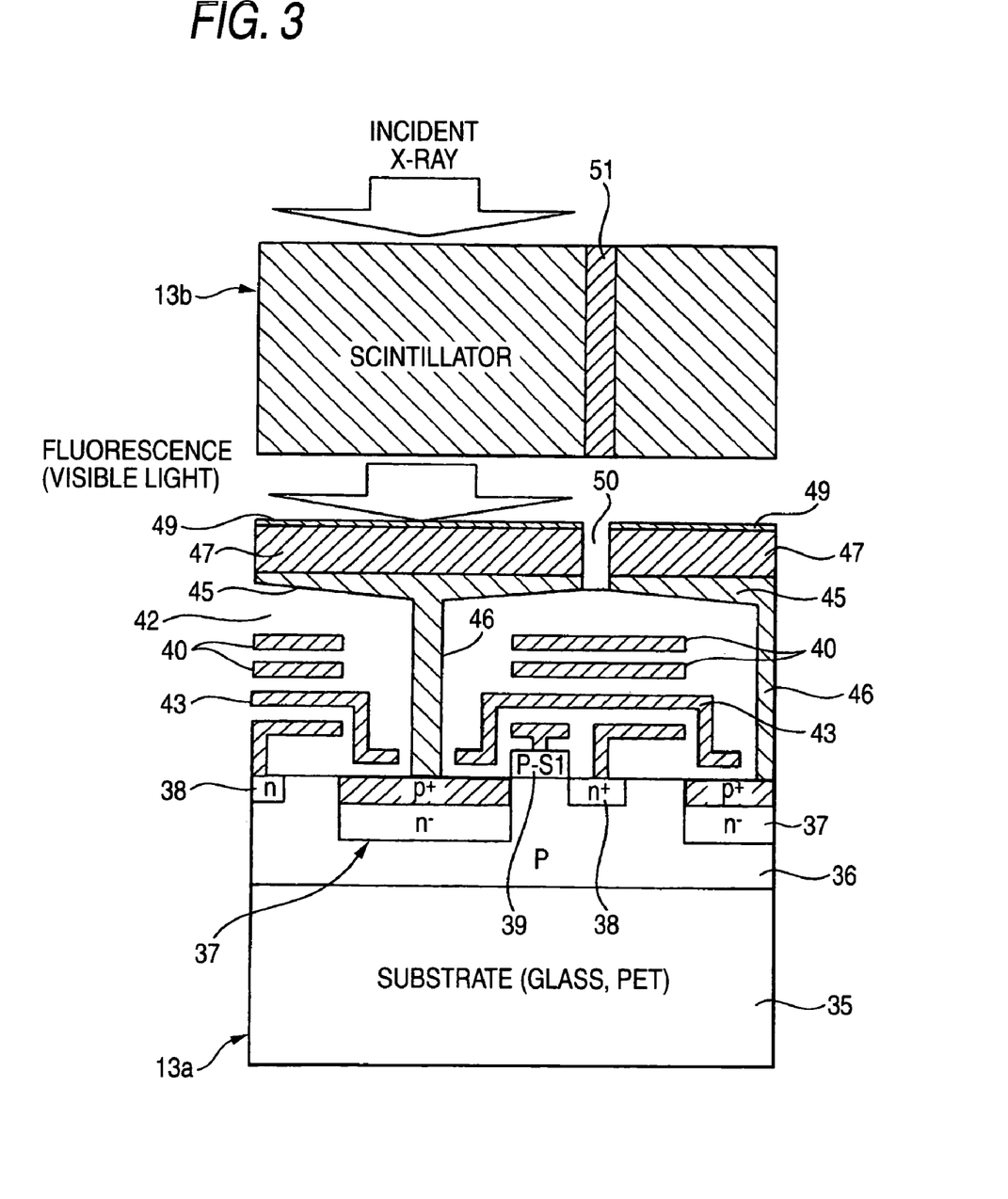
FIG. 3 is a schematic sectional view taken along a III-Ill line in FIG. 2.

FIG. 3 is a schematic sectional view taken along a III-III line in FIG. 2, which corresponds to a section of almost 1.5 pixel. FIG. 3 shows a section of the pixel in the higher-resolution image imaging area A, but a section of the pixel in the lower-resolution image imaging area B is similar to this.

The X-ray imaging device 13 in the present embodiment consists of an imaging device 13a and a scintillator 13b arranged over the imaging device 13a.

The imaging device 13a is formed on a flexible substrate 35. As the flexible substrate 35 used in the present embodiment, a glass substrate that can be formed thin and be curved or a flexible sheet formed by shaping the material such as polyethylene terephthalate (PET), or the like into a sheet is employed. As described above, there is no need to employ the flexible substrate if such substrate is the flat-shaped X-ray imaging device 13, and the semiconductor substrate itself or a thick glass substrate may be employed.

In the present embodiment, a p-type semiconductor layer 36 is formed on a surface of the flexible substrate 35. A diode portion explained later, the signal reading circuit 31, and the like are formed on the semiconductor layer 36 by using the technology to manufacture the TFT matrix on the liquid crystal substrate, or the like, as set forth in JP-A-5-158070, for example, or the technology to manufacture the organic EL device, or the like.

First, a diode portion 37 serving as a signal charge storage region is formed in locations on the surface portion of the semiconductor layer 36 respectively. Also, an n$^+$-region 38 constituting a part of the transistor of the signal reading circuit 31 is formed on the surface portion of the semiconductor layer 36. When a reading voltage is applied to a gate electrode 39 provided via a surface oxide layer (not shown) of the semiconductor layer 36, accumulated charges in the diode portions 37 are moved to the n$^+$-region 38 and then read out to the outside of the X-ray imaging device 13 by the signal reading circuit 31 (FIG. 2).

The signal reading circuit 31 and wiring layers 40 are shielded from a light by a light shielding layer 43 that is buried in an insulating layer 42 stacked on the surface portion of the semiconductor layer 36. Pixel electrode layers 45 are stacked on a surface of the insulating layer 42, and vertical wirings 46 for connecting the pixel electrode layers 45 and the diode portions 37 are provided upright. Then, photosensitive layers (photoelectric converting layers) 47 that are sensitive to a fluorescence emitted from the scintillator are stacked on the pixel electrode layers 45, and then a transparent opposing electrode layer 49 is stacked thereon. The imaging device 13a includes respective members from the flexible substrate 35 to the opposing electrode layer 49.

In the present embodiment, as shown in FIG. 3, since the photoelectric converting layer 47 is provided on the upper side of the semiconductor layer 36 constituting the signal reading circuit 31, the wiring 40 can be provided freely under the photoelectric converting layer 47. Therefore, as shown by a dotted line 40 in FIG. 2, even though the wirings 40 overlap with the light receiving area of each pixel, no problem is caused.

In contrast, when the configuration shown in FIG. 2 is constructed by the CCD image sensor or the CMOS image sensor in the related art, the signal charge storage portion 37 in FIG. 3 acts as the photodiode (photoelectric converting device). Therefore, the wiring 40 cannot be provided in the position that overlaps with this photodiode, and thus the imaging device cannot be designed freely.

In the imaging device 13a of the present embodiment, as shown in FIG. 3, a clearance (space) 50 for isolating adjacent photosensitive layers 47 (the electrode layers 45, 49) from each other is provided between the pixels at appropriate locations, and also a flexibility of the imaging device manufactured on the flexible substrate 35 is improved further. Thus, the X-ray imaging device 13 can be curved as shown in FIG. 1, and then can be arranged easily in the frame 15 of the X-ray CT apparatus. In this case, if a curvature to be curved is small and a radius of curvature is large, the clearance 50 is not always needed.

In the present embodiment, a separator 51 is inserted into the scintillator 13b, which is arranged over the imaging device 13a, between respective pixels not to lower a resolution of the captured image data. Since the scintillator 13b is basically made of a machinable ceramic substance, such scintillator is depicted as a rectangular prism in FIG. 3. Actually the scintillator 13b is shaped into a form whose upper area is slightly narrowed, and such scintillator is shaped into a curved form as a whole.

In the X-ray CT apparatus using the X-ray imaging device 13 constructed as above, when the tomogram of the subject on the stretcher (not shown) should be captured, the X-ray irradiator 12 and the X-ray imaging device 13 are turned while moving the stretcher in the center opening portion of the main body 11 of the X-ray CT apparatus 10.

The X-ray irradiated from the X-ray irradiator 12 to the subject is passed through the subject and is incident on the scintillator 13b. Then, the fluorescence is generated in response to a transmitted dose of the X-ray. When this fluorescence is incident into the imaging device 13a, an incident light is photoelectric-converted by the photosensitive layers (organic photoelectric converting layers) 47 (FIG. 3) and thus the hole-electron pairs are generated.

A voltage is applied to the photosensitive layers 47 between the pixel electrode layers 45-the the opposing electrode layer 49, as the case may be. A potential gradient is generated in the photosensitive layers 47 by this voltage, and the electrons out of the hole-electron pairs are moved to the pixel electrode layers 45 along this potential gradient. Then, the electrons flow through the vertical wirings 46 to the diode portions 37, and then the electrons are stored in the diode portions 37.

In the example illustrated in FIG. 3, the diode portions 37 are provided as the buried type such that these portions are not subjected to the influence of the lattice defect on the boundary. But a mere diode (capacitor) may be employed.

A charge storage timing applied to the diode portions 37 can be decided by either a voltage application to the photosensitive layers 47 or a resetting of the diode portions 37. In order to synchronize this charge storage timing with a scanning timing, desirably the method of reading the signal based on the MOS switching by executing sequentially steps of
(1) applying a high voltage to the photosensitive layers prior to the scan to discharge excess charges from the photosensitive layers,
(2) resetting the diode portions 37,
(3) applying a voltage to the photosensitive layers to generate a potential gradient, and
(4) starting the X-ray irradiation and starting the scan, should be employed.

The charges stored in the diode portions 37 are read out to a floating diffusion amplifier via a gate of a reading transistor in the signal reading circuit, and converted into a voltage. The signal can be output every pixel by reading the converted voltage. Also, the stored charges can be reset prior to the signal reading, as occasion demands (which is similar to the normal CMOS image sensor driving method).

In this case, the X-ray imaging device 13 can be slightly inclined from the slice direction in response to a moving speed of the stretcher and a turning speed of the scan. At that time, conveniently the spiral image data can be derived without stop of the stretcher.

In the case where the tomogram of the subject is captured in this manner, when the lower-resolution image may be used as the tomogram, a position of the X-ray receiving surface of the X-ray imaging device 13 is moved into the lower-resolution image imaging area B in FIG. 2 by the moving device 19. As a result, a scanning rate can be increased to a higher rate, and thus an exposure dose of the subject can be reduced.

When the higher-resolution image of the subject is captured, a position of the X-ray receiving surface of the X-ray imaging device 13 is moved into the higher-resolution image imaging area A in FIG. 2 by the moving device 19. As a result, the higher-resolution image of the subject can be captured.

Figure 4:
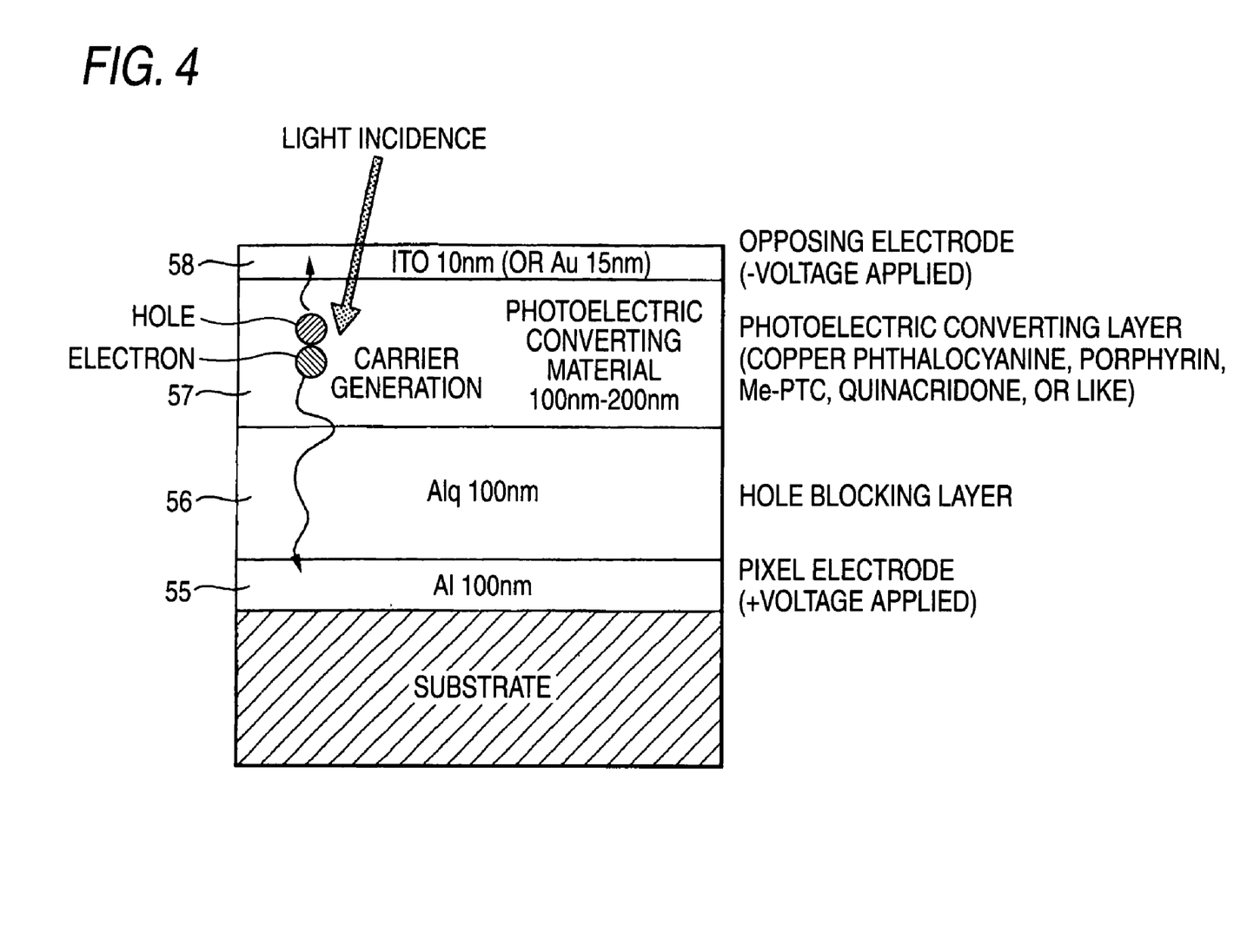
FIG. 4 is an explanatory view of a detailed section of a photosensitive layer.
Figure 5:
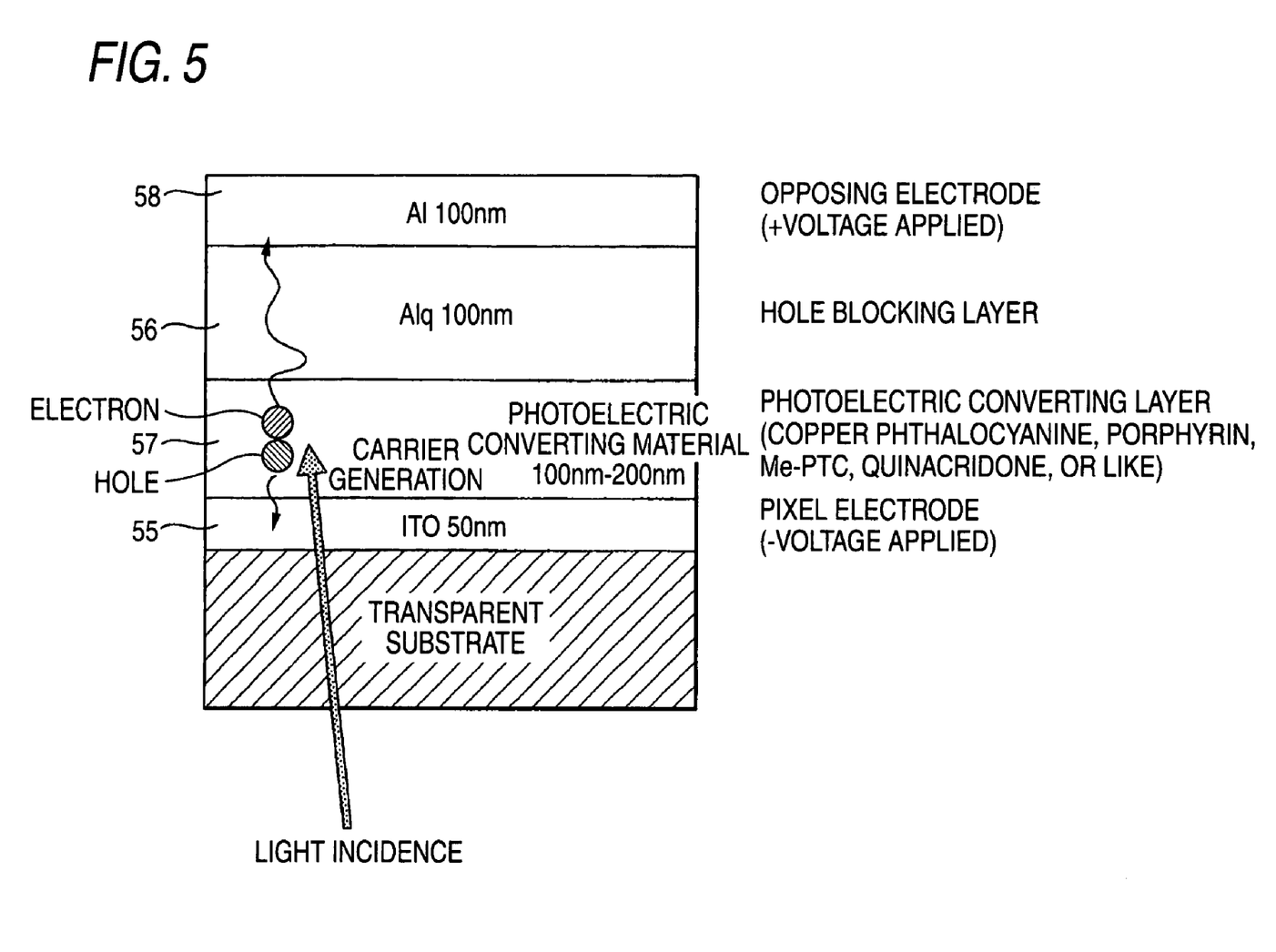
FIG. 5 is an explanatory view of a detailed section of another photosensitive layer.

FIG. 4 is an explanatory view of a detailed section of the photosensitive layer. In FIG. 3, the photosensitive layer is explained as the structure in which the photosensitive layer is put between the pixel electrode layer and the opposing electrode layer. But actually the structure illustrated in FIG. 4 should be employed preferably. Also, FIG. 4 shows the example in which light is incident from the opposite side to the substrate, while the case where light is incident from the substrate side when a transparent substrate is employed is shown in FIG. 5. Because explanations of the material and others are similar in both FIG. 4 and FIG. 5, explanation will be made of FIG. 4 only hereunder. Here, the diode portion, the vertical wiring, the signal reading circuit, the light shielding layer, and the like are omitted from FIG. 4 and FIG. 5.

In FIG. 4, a hole blocking layer 56 is formed of Alq on a pixel electrode layer 55 ("45" in FIG. 3) made of a thin aluminum, then a photosensitive layer 57 ("47" in FIG. 3) is formed by stacking photoelectric converting materials thereon, and then a transparent opposing electrode layer 58 ("49" in FIG. 3) is formed of ITO or Au thereon.

Films of the aluminum, the photoelectric converting materials, and Alq can be formed respectively by the vacuum deposition. A degree of vacuum should be set preferably to almost $10^{-4}$ Pa. When a voltage is applied between the pixel electrode layer 55 and the opposing electrode layer 58, a dark current caused by the injection of holes becomes large particularly and thus Alq is needed as the hole blocking layer 56.

The hole blocking layer 56 receives the electron carrier generated in the photosensitive layer (photoelectric converting layer) 57 and transports the electron carrier to the pixel electrode layer 55, while preventing the hole injection from the pixel electrode layer 55. Also, the hole blocking layer 56 has sensitivity although such sensitivity is small.

The opposing electrode (ITO, Au, or the like) 58 can be formed by the sputter, the electron beam deposition, the ion plating, or the like. In the case where an organic layer is employed as the photosensitive layer 57, normally a yield is extremely degraded due to a short-circuit when the ITO 58 is formed on the organic layer 57. In this case, when a thickness of ITO is set to almost 10 nm or less, a yield can be improved.

When the ITO heavily damages the organic layer 57, a thin layer of gold (Au) may be employed as the opposing electrode layer 58 although a light transmittance of Au is smaller than ITO. In this case, it is also desired that a thickness of Au is set to almost 15 nm or less.

When the photosensitive layer 57 has a thickness of about 100 nm, such photosensitive layer 57 can absorb 90 to 99% of an incident light including a reflection from the aluminum electrode layer 55. An applied voltage between the pixel electrode layer 55 and the opposing electrode layer 58 is set normally to almost 1 V to 30 V, and an external quantum efficiency at a maximum absorption wave is about 20 to 40% at the applied voltage of about 15 V. When the applied voltage is increased further more, a quantum efficiency can be increased but a S/N ratio is decreased because a dark current due to the carrier injection from the pixel electrode layer 55 is increased.

Since the photoelectric converting layer 57 formed of the organic material is deteriorated by an oxygen or a moisture, a sealing layer made of a silicon nitride, or the like must be formed on the opposing electrode layer 58 (in FIG. 3, the opposing electrode layer 59). At that time, the sealing layer should be formed by the low-damage sputter, the low-damage plasma CVD, or the like not to do the damage to the device.

As the material of the photosensitive layer 57 ("47" in FIG. 3), copper phthalocyanine, porphyrin, Me-PTC, quinacridone, or the like may be cited. It is decided based on a combination with the material of the scintillator what material should be employed as the photosensitive layer 57.

Figure 6A:
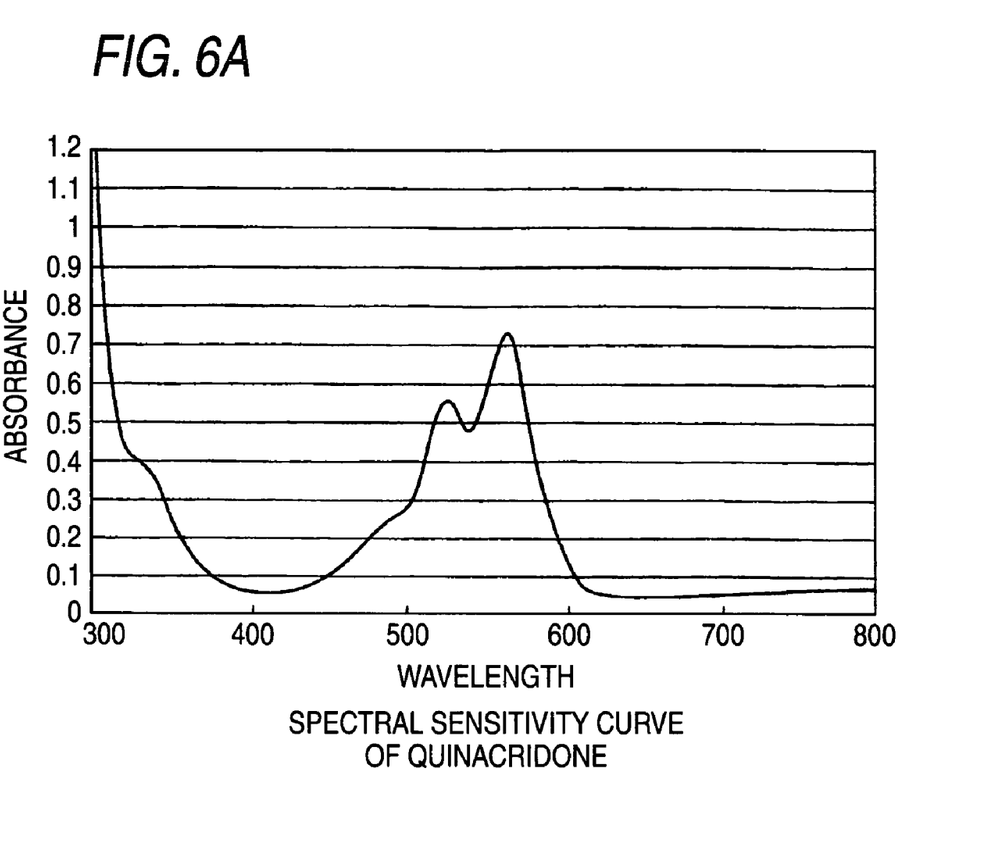
FIGS. 6A and 6B are views showing spectral sensitivity and a structural formula of quinacridone.
Figure 6B:
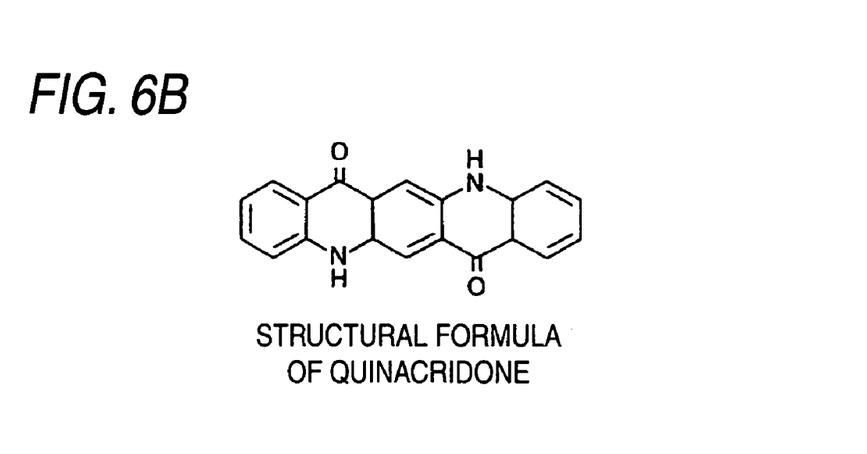

FIG. 6A shows the spectral sensitivity characteristic of quinacridone (FIG. 6A is the absorbance characteristic, but this absorbance characteristic is equivalent to the spectral sensitivity characteristic), and FIG. 6B shows the structural formula of quinacridone. This quinacridone has a sensitivity peak at two locations of around 550 nm and 300 nm or less. In this case, if this quinacridone is combined with the scintillator material (e.g., $CdWO_4$) whose luminous wavelength is near 550 nm, the photosensitive layer 47 made of quinacridone never receives the fluorescence whose wavelength is 300 nm or less. Therefore, no problem is caused.

In the X-ray CT apparatus, the number of image data to be processed becomes huge. Therefore, it is preferable that, when particularly the number of pixels in the higher-resolution image imaging area A is increased much more, the image data should be read from the X-ray imaging device 13 at a higher speed and then output to the image reconstruction calculating portion 22 (FIG. 1). A configuration of the X-ray imaging device 13 aiming at a high-speed reading is shown in FIG. 7.

The parallel reading is effective to accelerate a reading speed of the signal reading circuit constructed by CMOS circuits. Therefore, in the embodiment shown in FIG. 12, the number of signal reading lines 61 (the vertical reading lines in FIG. 7) of the signal reading circuits are increased rather than the embodiment shown in FIG. 2 such that the image can be read simultaneously from four pixels in the vertical direction.

Also, when the number of signal reading lines 61 is increased, the number of output signal lines is also increased in proportion to that number. Therefore, the output signals are converted into digital signals by AD converters 62, and then the multiple digital signals are read into an output signal bus 63, so that the number of output signal lines is reduced. The parallel bus may be employed as the output signal bus 63, but the number of output signal lines can be reduced further when the serial bus is employed as the output signal bus.

Figure 7:
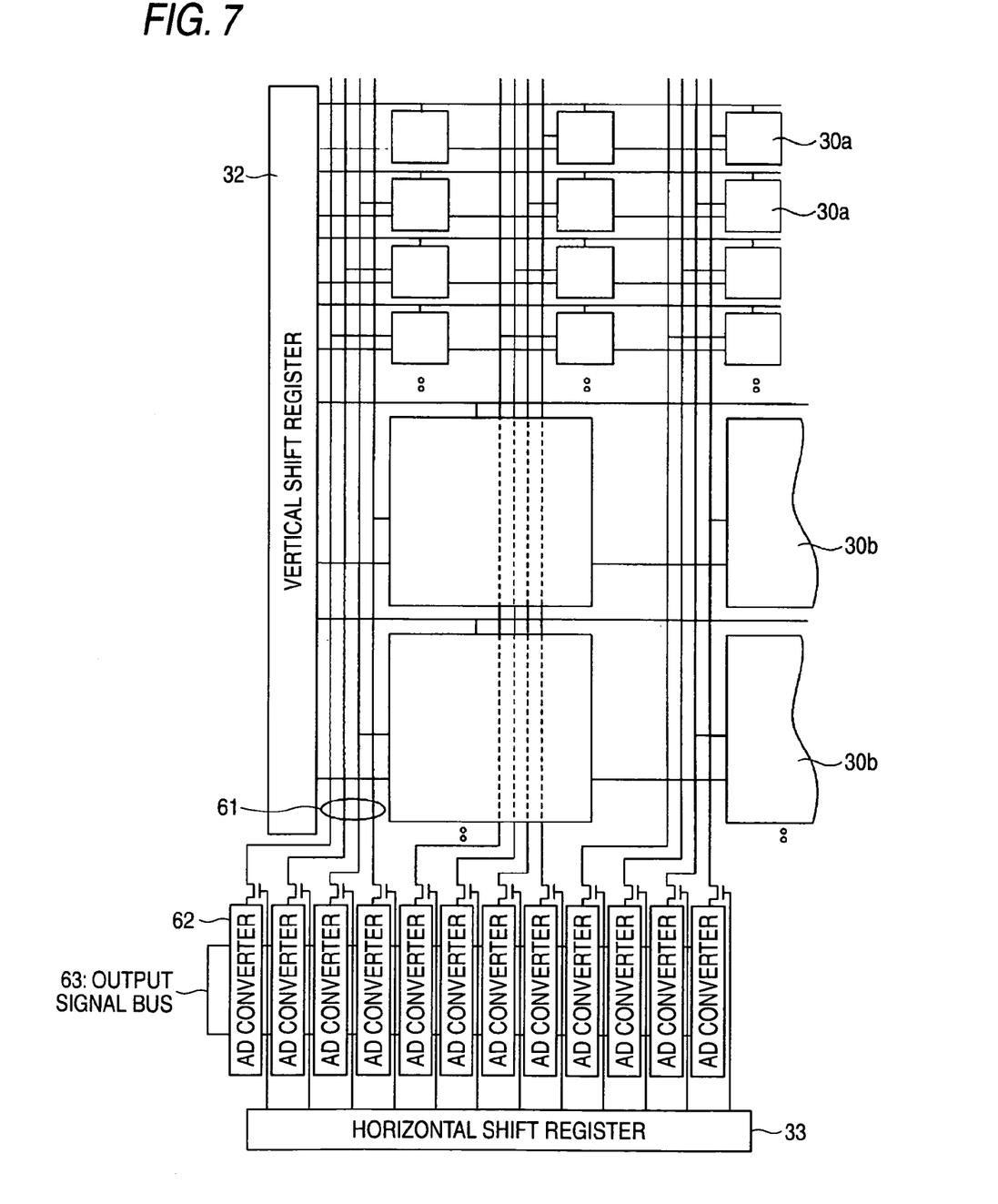
FIG. 7 is a configurative view of a higher-speed readable X-ray imaging device in an exemplary embodiment instead of FIG. 2.

In FIG. 7 (also in FIG. 2), the number of pixels 30a, 30b are reduced in the illustration. It is of course that actually a larger number of pixels 30a, 30b are present.

In the above embodiment, the higher-resolution image imaging area A and the lower-resolution image imaging area B are provided to the X-ray imaging device 13. Also, a middle-resolution image imaging area may be provided.

Figure 8:
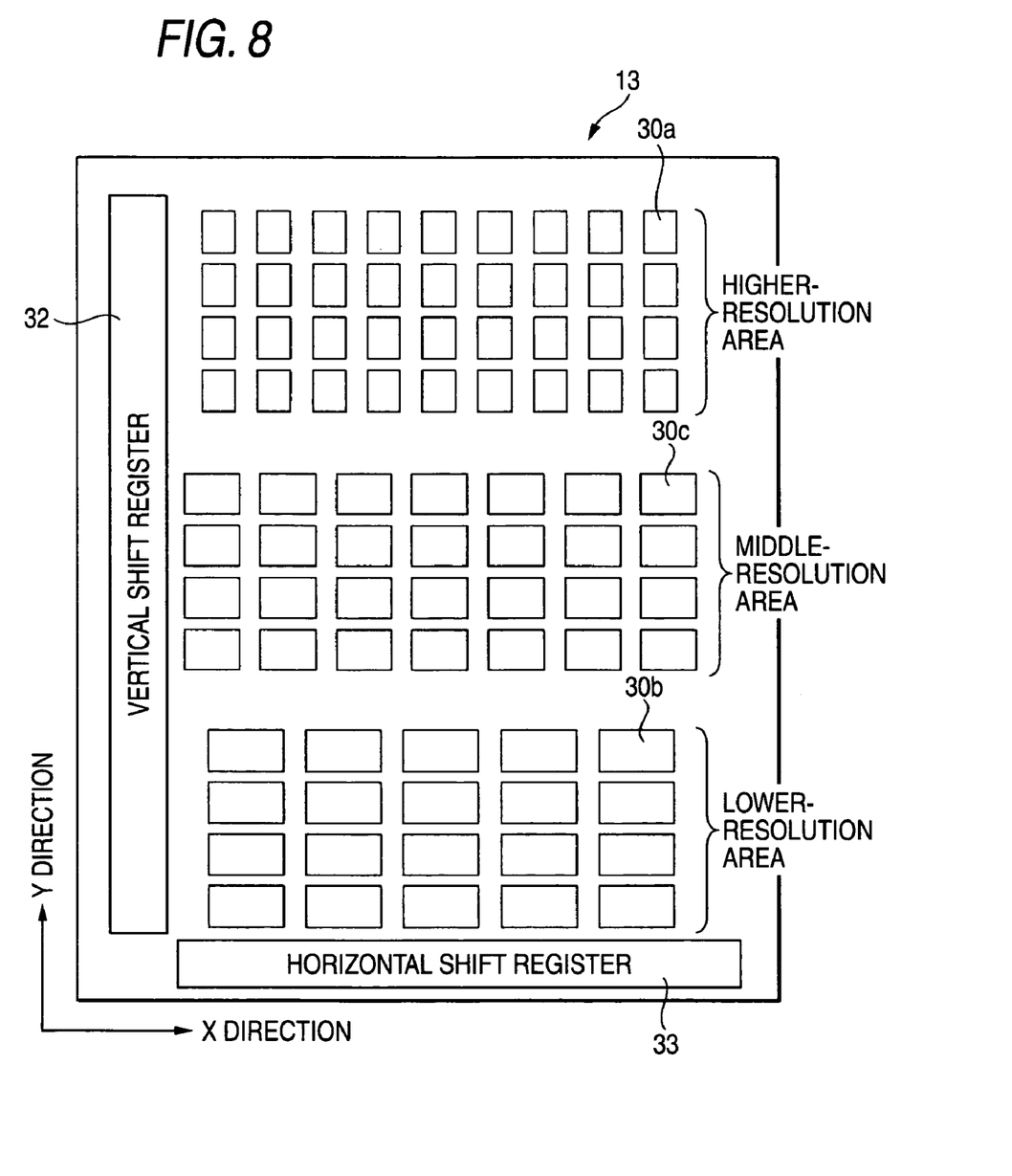
FIG. 8 is a schematic plan view of an X-ray imaging device according to another exemplary embodiment of the present invention.
Figure 9:
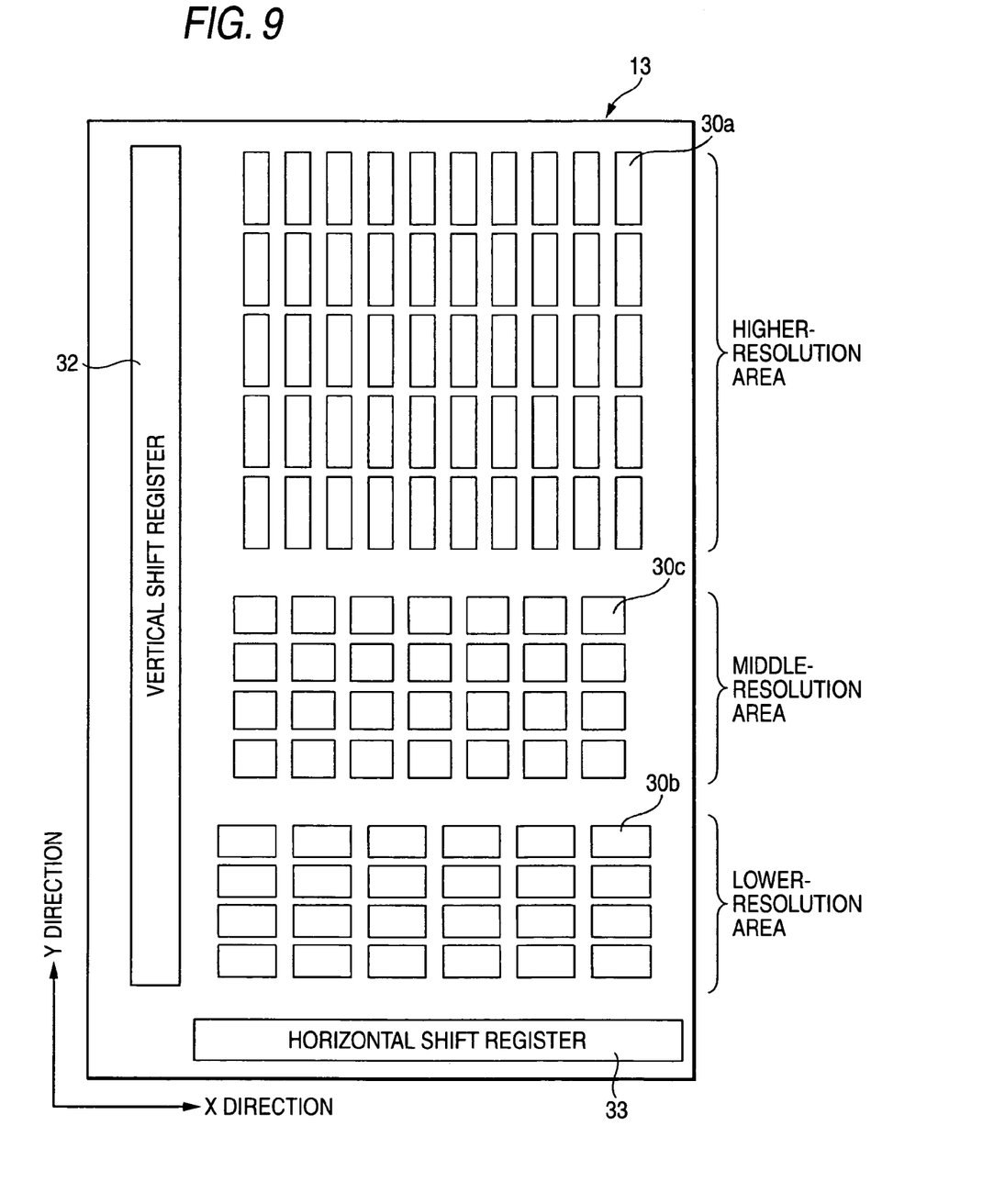
FIG. 9 is a schematic plan view of an X-ray imaging device according to another embodiment exemplary of the present invention.

FIG. 8 and FIG. 9 are a schematic plan view of an X-ray imaging device in which the higher-resolution image imaging area, the middle-resolution image imaging area, and the lower-resolution image imaging area are provided, respectively. In FIG. 8 and FIG. 9, only pixels 30a in the higher-resolution image imaging area, pixels 30c in the middle-resolution image imaging area, pixels 30b in the lower-resolution image imaging area, the vertical shift register 32, and the horizontal shift register 33 are shown, but the wirings are omitted from the illustration. In this case, as described above, since the wiring layers can be formed below the photoelectric converting layer in the imaging device in which the photoelectric converting layers are stacked, there is no trouble even when respective pixels overlap with the wirings, and the wirings can be designed freely. In other words, the alignments of pixels whose resolutions are changed are provided previously only in the upper photoelectric converting layer, and then the pixels having a constant resolution (pixel interval) respectively can be provided in the lower wiring layers.

In the X-ray imaging device 13 of the present embodiment shown in FIG. 8, dimensions and alignment pitches of respective pixels 30a, 30b, 30c in the Y direction (slice direction) are set equal respectively, but their resolutions are changed by changing their dimensions and alignment pitches in the X direction (scan direction). A pixel pitch between the pixels 30a in the X direction is finest, and a pixel pitch between the pixels 30c in the X direction is next finest.

In this manner, the resolution can be changed by changing the dimensions and the alignment pitches only in either of the X direction and the Y direction. However, because he pixel pitch becomes finer, particularly the pixel pitch between the pixels 30a provided in he higher-resolution image imaging area becomes finer (a dimension in that direction becomes smaller), the sensitivity of the pixel 30a is degraded.

In this case, it is preferable that the light receiving areas of the pixels 30a, 30b, 30c in respective resolution areas should be kept almost equal by changing the pixel pitch (pixel dimension) in both the X direction and the Y direction. FIG. 9 is a schematic plan view of the X-ray imaging device 13 showing that example wherein the pixel area is secured by extending a dimension of the pixel 30a in the Y direction and thus a reduction of sensitivity is prevented.

In order to switch the resolution of the X-ray imaging device 13, there are the method of using selectively the slice direction (row) of the X-ray imaging device 13, the method of using this method and the focusing made by the collimator in the X-ray generator apparatus in combination, the method of moving the X-ray imaging device 13 by a pixel pitch not to make the operation such as the focusing of the X-ray irradiation, and the like. As the moving method, there are a stepping motor, a drive by using a piezoelectric device, and the like.

As described above, according to respective embodiments of the present invention, the images can be captured at different resolutions by a single X-ray imaging device. Therefore, the higher-resolution image data can be acquired, and also an exposure dose of the subject can be reduced by increasing a scanning rate to a higher rate when the image data is acquired at the lower-resolution.

In the X-ray imaging device of the above embodiment, the signal reading circuit consisting of a three-transistor arrangement or a four-transistor arrangement used in the CMOS image sensor in the related art is employed as the signal reading means. It is needless to say that the configuration using the charge transferring path in the CCD image sensor in the related art may be employed as the signal reading means.

An embodiment of the invention is useful to the X-ray CT apparatus, or the like because the X-ray image can be captured while switching a higher-resolution and a lower-resolution.

While the invention has been described with reference to the exemplary embodiments, the technical scope of the invention is not restricted to the description of the exemplary embodiments. It is apparent to the skilled in the art that various changes or improvements can be made. It is apparent from the description of claims that the changed or improved configurations can also be included in the technical scope of the invention.

This application claims foreign priority from Japanese Patent Application No. 2005-288864, filed Sep. 30, 2005, the entire disclosure of which is herein incorporated by reference.

What is claimed is:

1. A resolution-variable X-ray imaging device comprising:
   a scintillator that receives an X-ray through a subject to emit fluorescence; and
   an imaging portion comprising:
      a plurality of pixels aligned at pixel intervals on a light receiving surface of the imaging portion, each of the pixels receiving the fluorescence and converting the fluorescence into an electric signal;
      a higher-resolution imaging area in which the pixels are aligned at a pixel interval;
      a lower-resolution imaging area in which the pixels are aligned at a pixel interval longer than the pixel interval of the higher-resolution imaging area;
      a p-type semiconductor layer formed on a surface of a flexible substrate comprising one of glass and a polymer;
      a charge storage diode formed on a surface portion of the p-type semiconductor layer;
      an $n^+$-region constituting a part of a transistor of a signal reading circuit formed on the surface portion of the p-type semiconductor layer; and
      an insulating layer formed on the surface portion of the p-type semiconductor layer,
   wherein the areas of the imaging portion are selectable according to a desired image resolution.

2. The resolution-variable X-ray imaging device according to claim 1, wherein the imaging portion further comprises a photosensitive layer comprising an organic material that photoelectrically converts incident light.

3. The resolution-variable X-ray imaging device according to claim 2, wherein the imaging portion further comprises:
   a light shielding layer buried in the insulating layer; and
   a pixel electrode layer formed on a surface of the insulating layer.

4. The resolution-variable X-ray imaging device according to claim 3, wherein the imaging portion further comprises:
   a hole blocking layer formed on the pixel electrode layer, the photosensitive layer being formed by stacking photoelectric converting material on the hole blocking layer and being isolated from a second photosensitive layer by a clearance provided by the pixels; and
   a transparent opposing electrode layer formed on the photosensitive layer,
   wherein the pixel electrode layer is connected to the charge storage diode by vertical wirings and a sealing layer of silicon nitride is formed on the transparent opposing electrode layer.

5. The resolution-variable X-ray imaging device according to claim 4, wherein the transparent opposing electrode layer comprises a thin layer of gold and is less than 15 nm thick.

6. The resolution-variable X-ray imaging device according to claim 2, wherein the scintillator comprises a material emitting the fluorescence, and
   wherein a peak wavelength of the fluorescence coincides, in a wavelength range, with a peak wavelength of a photo sensitivity of the organic material in the photosensitive layer.

7. The resolution-variable imaging device according to claim 2, wherein the photosensitive layer comprises quinacridone.

8. The resolution-variable X-ray imaging device according to claim 1, wherein each of the higher-resolution imaging area and the lower-resolution imaging has pixel pitches different in two directions perpendicular to each other.

9. The resolution-variable X-ray imaging device according to claim 8, wherein each of the pixels in each of the higher-resolution imaging area and the lower-resolution imaging has a common light receiving area.

10. The resolution-variable imaging device according to claim 1, wherein the signal reading circuit comprises a number of signal reading lines such that an image can be read simultaneously from four pixels in a vertical direction.

11. The resolution-variable imaging device according to claim 1, wherein the imaging portion further comprises a middle-resolution imaging area in which the pixels are aligned at a pixel interval that is longer than the pixel interval of the higher-resolution imaging area and shorter than the pixel interval of the lower-resolution imaging area.

12. An X-ray CT apparatus comprising:
    an X-ray irradiator that irradiates a subject with an X-ray;

a resolution-variable X-ray imaging device, the X-ray imaging device being a positioned opposite to the X-ray irradiator through the subject, the X-ray imaging device comprising an imaging portion comprising:
- a higher-resolution imaging area in which the pixels are aligned at a pixel interval;
- a lower-resolution imaging area in which the pixels are aligned at a pixel interval longer than the pixel interval of the higher-resolution imaging area;
- a p-type semiconductor layer formed on a surface of a flexible substrate comprising one of glass and a polymer;
- a charge storage diode formed on a surface portion of the p-type semiconductor layer;
- an $n^+$-region constituting a part of a transistor of a signal reading circuit formed on the surface portion of the p-type semiconductor layer; and
- an insulating layer formed on the surface portion of the p-type semiconductor layer; and a driving unit that turns integrally the X-ray irradiator and the resolution-variable X-ray imaging device round the subject in such a state that the resolution-variable X-ray irradiator and the X-ray imaging device are opposed to each other, wherein the areas of the imaging portion are selectable according to a desired image resolution.

13. The X-ray CT apparatus according to claim 12, wherein the resolution-variable X-ray imaging device has a curved shape.

14. A method of manufacturing a resolution-variable X-ray imaging device, comprising:
- forming and aligning a plurality of pixels at a narrow pitch in a higher-resolution imaging area;
- forming and aligning a plurality of pixels at a wide pitch in a lower-resolution imaging area, the lower-resolution imaging area pixels comprising a light receiving area wider than a light receiving area of the higher-resolution imaging area pixels;
- forming a p-type semiconductor layer on a surface of a flexible substrate comprising one of glass and a polymer;
- forming a charge storage diode and a signal reading circuit on a bottom portion of the pixels and a surface portion of the p-type semiconductor layer, the signal reading circuit comprising at least three transistors used in a complementary metal-oxide-semiconductor image sensor;
- forming an $n^+$-region constituting a part of one of said at least three transistors of the signal reading circuit on the surface portion of the p-type semiconductor layer;
- forming an insulating layer formed on the surface portion of the p-type semiconductor layer; and
- forming a scintillator over the imaging portion, the scintillator including a separator between the pixels, wherein the signal reading circuit is connected to a vertical shift register and a horizontal shift register.

* * * * *